United States Patent [19]

Rizkalla et al.

[11] Patent Number: 5,504,052
[45] Date of Patent: Apr. 2, 1996

[54] SILVER CATALYST PREPARATION

[75] Inventors: Nabil Rizkalla, Riverdale; William Armstrong, Ramsey, both of N.J.

[73] Assignee: Scientific Design Company, Inc., Little Ferry, N.J.

[21] Appl. No.: 348,340

[22] Filed: Dec. 2, 1994

[51] Int. Cl.$^6$ .................................................. B01J 23/50
[52] U.S. Cl. .......................... 502/347; 502/243; 502/348
[58] Field of Search .................................... 502/243, 347, 502/348

[56] References Cited

U.S. PATENT DOCUMENTS

| | | | |
|---|---|---|---|
| 3,702,259 | 11/1972 | Nielsen | 117/37 R |
| 3,962,136 | 6/1976 | Nielsen et al. | 252/454 |
| 4,471,071 | 9/1984 | Rebsdat et al. | 502/347 |
| 4,761,394 | 8/1988 | Lauritzen | 502/348 |
| 4,766,105 | 8/1988 | Lauritzen | 502/216 |
| 4,837,194 | 6/1989 | Hayden | 502/348 |
| 5,077,256 | 12/1991 | Yamamoto et al. | 502/243 |
| 5,081,096 | 1/1992 | Monnier et al. | 502/348 |
| 5,374,748 | 12/1994 | Rizkalla | 549/534 |

Primary Examiner—E. Rollins Cross
Assistant Examiner—Timothy H. Meeks
Attorney, Agent, or Firm—William C. Long

[57] ABSTRACT

A silver catalyst for ethylene oxidation to ethylene oxide is prepared by impregnating an inert support with a silver/amine solution and calcining the impregnated support at 300°–5000° C., the catalyst being maintained under an inert atmosphere at temperatures of 250° C. or higher, preferably at 100° C. or higher.

3 Claims, 3 Drawing Sheets

SILVER CATALYST PREPARATION

BACKGROUND OF THE INVENTION

1. Field of the Invention

The present invention relates to the preparation of a supported silver catalyst, which is useful for the vapor phase oxidation of ethylene to ethylene oxide, by a process whereby a support is impregnated with a silver salt/amine solution and the resultant impregnated support is calcined under controlled conditions of temperature and inert atmosphere to produce the silver catalyst.

2. Description of the Prior Art

Methods are known for the preparation of supported silver catalysts useful for the vapor phase oxidation of ethylene to ethylene oxide, which methods involve impregnating a support such as alumina with a silver salt/amine solution. U.S. Pat. No. 3,702,359 is illustrative of such procedures. The preparation of silver catalysts which also contain alkali metal promoters by analogous procedures is shown, for example, in U.S. Pat. No. 3,962,136. Still further, similar procedures for the preparation of silver catalysts promoted alkali metal and rhenium and also with a co-promoter selected from sulfur, molybdenum, tungsten, chromium and mixtures are shown in U.S. Pat. No. 4,766,105.

Catalyst preparation by these prior art procedures has involved impregnating a support with the silver/amine solution which may contain the various promoters, and thereafter heating the impregnated support in a forced air oven up to a temperature of about 275° C. in order to reduce the silver to metallic silver and to separate volatiles from the catalyst.

In U.S. Pat. No. 5,444,034, a continuation of abandoned application Ser. No. 08/024,477 filed Feb. 25, 1993 which relates to silver catalyst preparation wherein a support is impregnated with a hydrocarbon solution of a silver salt of an organic acid such as neodecanoic acid, activation in stages up to a temperature of 500° C. is shown under an inert gas such as nitrogen. A divisional filing has issued as U.S. Pat. No. 5,374,748.

BRIEF DESCRIPTION OF THE INVENTION

In accordance with the present invention an improved method is provided for the preparation of silver catalysts useful for the vapor phase oxidation of ethylene to ethylene oxide. A conventional support such as alumina is impregnated with a silver/amine impregnating solution. Subsequently, the impregnated support is calcined at a temperature in the range of about 300° C.–500° C. for a time sufficient to reduce the silver component to metallic silver and to remove volatile decomposition products from the silver containing support. A critical feature of the instant catalyst preparation procedure is that contact of the silvercontaining support with an oxygen containing atmosphere is avoided at least at temperatures above about 250° C., and preferably at temperatures in excess of 100° C. Both during the period when the impregnated support is heated to and maintained at 300°–500° C., and during cooling of the calcined catalyst from 300°–500° C. to 200° C. or lower, preferably 100° C. or lower, an inert atmosphere such as nitrogen or helium is maintained in contact with the silver containing support.

DETAILED DESCRIPTION

Figure 2:
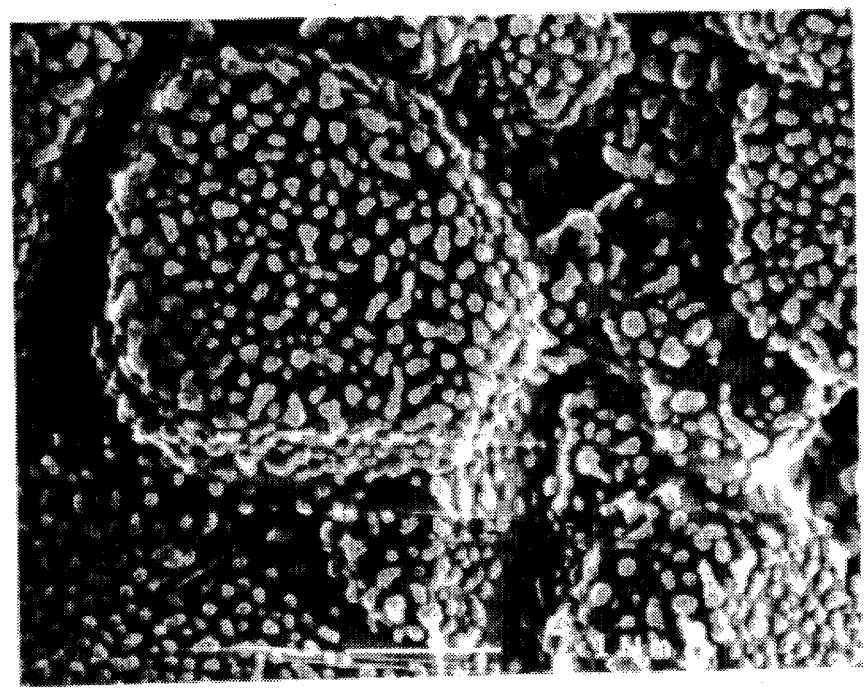
FIG. 2 is a scanning electron micrograph of a silver catalyst similarly prepared but calcined at 270° C. under air in accordance with prior art procedures.

Preferred catalysts prepared in accordance with this invention contain up to about 20% by weight of silver, expressed as metal, deposited upon the surface and throughout the pores of a porous refractory support. Silver contents higher than 20% by weight of total catalyst are effective, but result in catalysts which are unnecessarily expensive. Silver contents, expressed as metal, of about 5–15% based on weight of total catalyst are preferred, while silver contents of 8–13% are especially preferred.

Catalysts may be made with supports comprising alumina, silica, silica-alumina or combinations thereof. Preferred supports are those containing principally alpha-alumina, particularly those containing up to about 15 wt % silica. Especially preferred supports have a porosity of about 0.1–1.0 cc/g and preferably about 0.2–0.7 cc/g. Preferred supports also have a relatively low surface area, i.e. about 0.2–2.0 m$^2$/g, preferably 0.4–1.6 m$^2$/g and most preferably 0.5–1.3 m$^2$/g as determined by the BET method. See J.A. Chem. Soc. 60, 3098–16 (1938). Porosities are determined by the mercury porosimeter method; see Drake and Ritter, "Ind. Eng. Chem. Anal Ed.," 17, 787 (1945). Pore and pore diameter, distributions are determined from the surface area and apparent porosity measurements.

For use in commercial ethylene oxide production applications, the supports are desirably formed into regularly shaped pellets, spheres, rings, etc. Desirably, the support particles may have "equivalent diameters" in the range from 3–10 mm and preferably in the range of 4–8 mm, which are usually compatible with the internal diameter of the tubes in which the catalyst is placed. "Equivalent diameter" is the diameter of a sphere having the same external surface (i.e. neglecting surface within the pores of the particle) to volume ration as the support particles being employed.

As an essential feature of the invention, the silver is added to the support by immersion of the support into a silver/amine impregnating solution or by the incipient wetness technique. The silver containing liquid penetrates by absorption, capillary action and/or vacuum into the pores of the support. A single impregnation or a series of impregnations, with or without intermediate drying, may be used, depending in part upon the concentration of the silver salt in the solution. To obtain catalyst having silver contents within the preferred range, suitable impregnating solutions will generally contain from 5–50 wt % silver, expressed as metal. The exact concentrations employed, of course, will depend upon, among other factors, the desired silver content, the nature of the support, the viscosity of the liquid, and solubility of the silver compound.

Impregnation of the selected support is achieved in a conventional manner. The support material is placed in the silver solution until all of the solution is absorbed by the support. Preferably the quantity of the silver solution used to impregnate the porous support is no more than is necessary to fill the pore volume of the porous support.

The impregnating solution, as already indicated, is characterized as a silver/amine solution, preferably such as is fully described in U.S. Pat. No. 3,702,259 the disclosure of which is incorporated herein by reference . Alkali metal promoters, most preferably cesium, and the impregnation procedures described in U.S. Pat. No. 3,962,136 are advantageously employed as are the rhenium and other co-promoters and impregnation procedures described in U.S. Pat. Nos. 4,761,394 and 4,766,105 the disclosures of all of which are hereby incorporated by reference.

Known prior procedures of predeposition, co-deposition and postdeposition of various promoters can be employed. In the case of postdeposition, this is preferably carried out after calcination of the silver catalyst.

After impregnation, any excess impregnating solution is separated and the impregnated support is calcined or activated. The calcination is accomplished by heating the impregnated support, preferably at a gradual rate, to a temperature in the range 300°–500° C. for a time sufficient to convert the contained silver to silver metal and to decompose the organic materials and remove the same as volatiles.

It is essential in accordance with this invention that the impregnated support be maintained under an inert atmosphere while it is above 250° C. during the entire procedure. While not wishing to be bound by theory, it is believed that at temperatures of 250° C. and higher oxygen is absorbed in substantial quantities into the bulk of the silver where it has an adverse effect on the catalyst characteristics.

Catalysts prepared by the procedures above have improved performance, especially stability, for use in the production of ethylene oxide by the vapor phase oxidation of ethylene with molecular oxygen. These usually involve reaction temperatures of about 150° C. to 400° C., usually about 200° C. to 300° C., and reaction pressures in the range of from 0.5 to 35 bar. Reactant feed mixtures contain 0.5 to 20% ethylene and 3 to 15% oxygen, with the balance comprising comparatively inert materials including such substances as nitrogen, carbon dioxide, methane, ethane, argon and the like. Only a portion of the ethylene usually is reacted per pass over the catalyst and after separation of the desired ethylene oxide product and the removal of appropriate purge stream sand carbon dioxide to prevent uncontrolled build up of inerts and/or by-products, unreacted materials are returned to the oxidation reactor.

The following examples illustrate the benefits of calcination in inert atmosphere according to the invention.

| Silver Solution Preparation Chemical Compounds utilized (parts by weight): | |
|---|---|
| Silver Oxide | 688 |
| Oxalic Acid | 369 |
| Ethylene diamine | 409 |
| Deionized water | 2340 |
| 4% Cesium hydroxide in water | |

Silver oxide (679 parts) was mixed with water, at room temperature, followed by the gradual addition of the oxalic acid. The mixture was stirred for 15 minutes and at that point the color of the black suspension of silver oxide was changed to the gray/brown color of silver oxalate. The pH of the mixture was measured and was adjusted to a pH higher than 7 via adding an additional amount of silver oxide. The total amount of silver oxide added was 688 parts.

The suspension was allowed to settle and this was followed by decanting most of the clear liquid that developed on top of the mixture. The container was placed in an ice bath and stirred while ethylene diamine was added slowly to maintain the reaction temperature lower than 33° C. After the addition of all the ethylene diamine the solution was filtered at room temperature. The clear filtrate was utilized as a silver/amine stock solution for the catalyst preparation. In the following examples, parts are by weight unless otherwise specified.

EXAMPLE 1

Preparation Procedure

The support used for this preparation was obtained from Norton Company and was made primarily of α-alumina in the form of 5/16" cylinders. The support has a surface area of 0.55 m$^2$/g pore volume of 0.3 cc/g, and median pore diameter of 1.5 μ. about 1110 parts of the silver solution was mixed with:

1. 11.88 parts of CsOH solution,
2. 13.9 parts of ammonium perrehanate, (3.77% Re in water), and
3. 1.8 parts of ammonium sulfate, (5% S in water).

The mixture was stirred to assure homogeneity, then added to 2500 parts of the support. The wet catalyst was mixed for ten minutes and then calcined.

Calcination, the deposition of silver compound, was induced by heating the catalyst up to the decomposition temperature of the silver salt. This was achieved via heating in a furnace that has several heating zones in a controlled atmosphere. The catalyst was loaded on a moving belt that entered the furnace at ambient temperature. The temperature was gradually increased as the catalyst passed from one zone to the next and was increased, up to 400° C., as the catalyst passed through seven heating zones. After the heating zones the belt passed through a cooling zone that gradually cooled the catalyst to a temperature lower than 100° C. The total residence time in the furnace was 22 minutes. The atmosphere of the furnace was controlled through flow of nitrogen to the different heating zones. Nitrogen was passed upwardly through the catalyst in each zone to aid in the removal of volatiles and to provide and atmosphere essentially free of oxygen.

Figure 1:
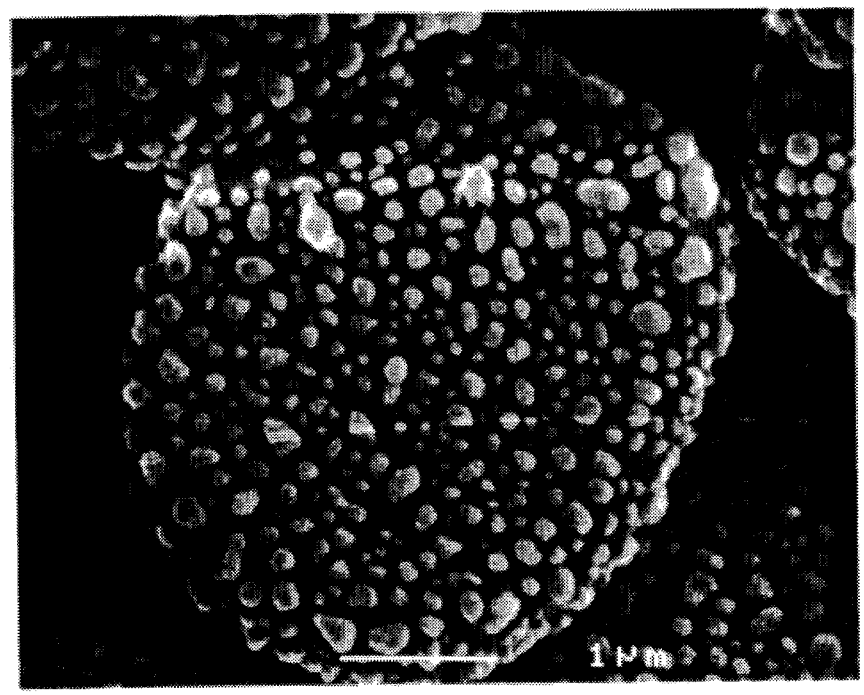
FIG. 1 is a scanning electron micrograph of a silver catalyst of the invention calcined at 400° C. under nitrogen.

FIG. 1 is an electron micrograph of this catalyst.

EXAMPLE 2

(Comparative)

Catalyst preparation was the same as Example 1 except that calcination was conducted in air and to a maximum temperature of 270° C. FIG. 2 is an electron micrograph of this catalyst.

EXAMPLE 3

(Comparative)

Figure 3:
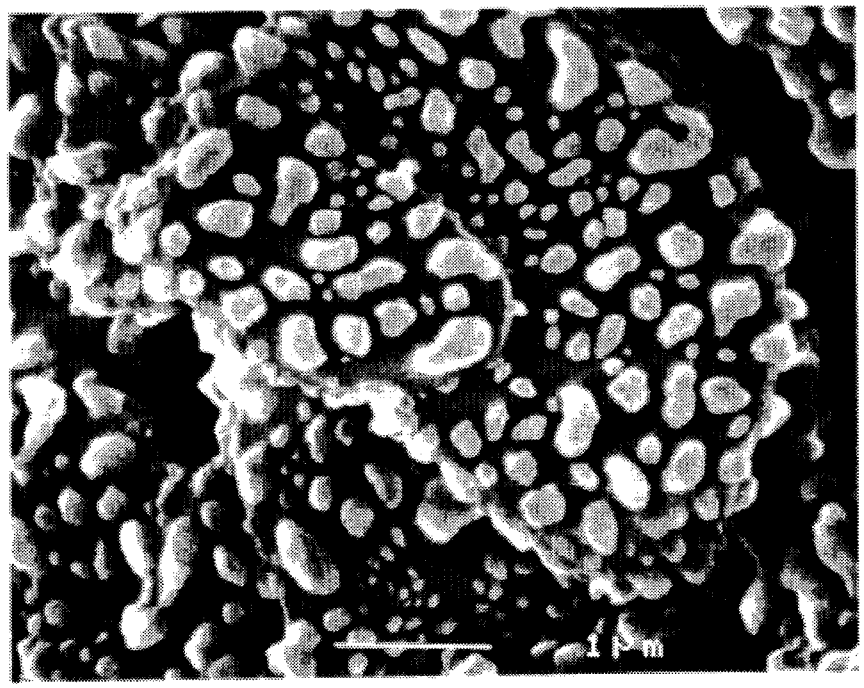
FIG. 3 is a scanning electron micrograph of a silver catalyst similarly prepared but calcined under air at 400° C.

Catalyst preparation was identical to Example 1 except the calcination was conducted in air and to a maximum temperature of 400° C. FIG. 3 is an electron micrograph of this catalyst.

EXAMPLE 4

Preparation Procedure

The support used for this preparation was obtained from Norton Company and was made primarily of α-alumina in the form of 5/16" cylinders. The support has a surface area of 0.55 m²/g pore volume of 0.3 cc/g, and median pore diameter of 1.5 μ. about 1110 parts of the silver solution was mixed with 8.56 parts of CsOH solution. The mixture was stirred to assure homogeneity then added to 2500 parts of the support. The wet catalyst was mixed for ten minutes and then calcined.

Calcination, the deposition of silver compound, was induced by heating the catalyst up to the decomposition temperature of the silver salt. This was achieved via heating in a furnace having several heating zones in a controlled atmosphere. The catalyst was loaded on a moving belt that entered the furnace at ambient temperature. The temperature was gradually increased as the catalyst passed from one zone to the next and was increased, up to 400° C., as the catalyst passed through seven heating zones. After the heating zones the belt passed through a cooling zone that gradually cooled the catalyst to a temperature lower than 100° C. The total residence time in the furnace was 22 minutes.

Figure 4:
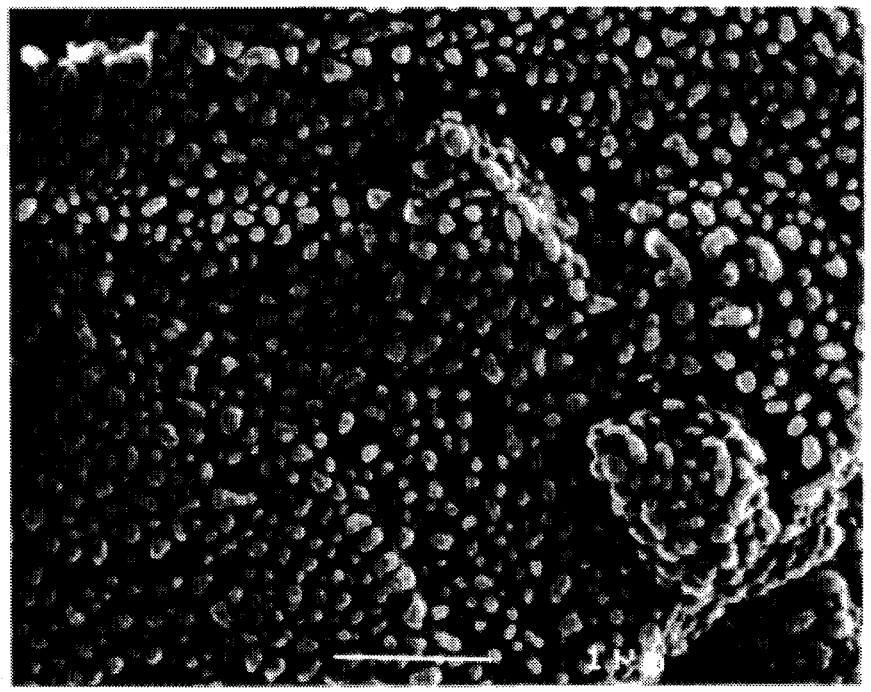
FIG. 4 is a scanning electron micrograph of a silver catalyst of the invention calcined at 400° C. under nitrogen.

The atmosphere of the furnace was controlled by nitrogen flow to the different heating zones. Nitrogen was passed upwardly through the catalyst in each zone to aid in the removal of volatiles and to provide an atmosphere essentially free of oxygen. FIG. 4 is an electron micrograph of this catalyst.

EXAMPLE 5

Preparation procedure

Figure 5:
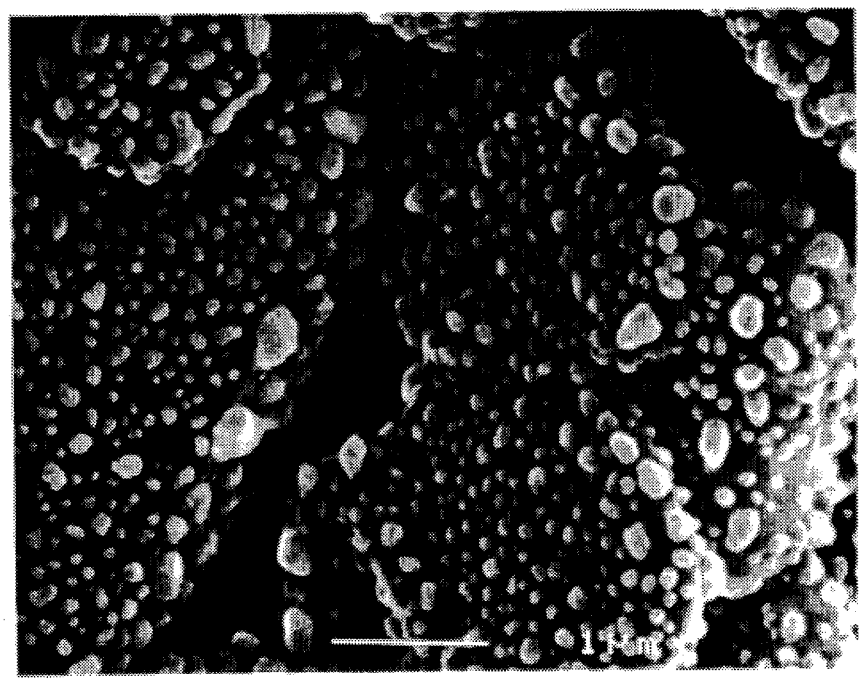
FIG. 5 is a scanning electron micrograph of a silver catalyst prepared in a similar way to that of FIG. 4 but calcined at 270° C. under air.

Catalyst preparation was identical to Example 4 except the calcination was induced in air and to a maximum temperature of 270° C. FIG. 5 is an electron micrograph of this catalyst.

EXAMPLE 6

(Comparative)

Figure 6:
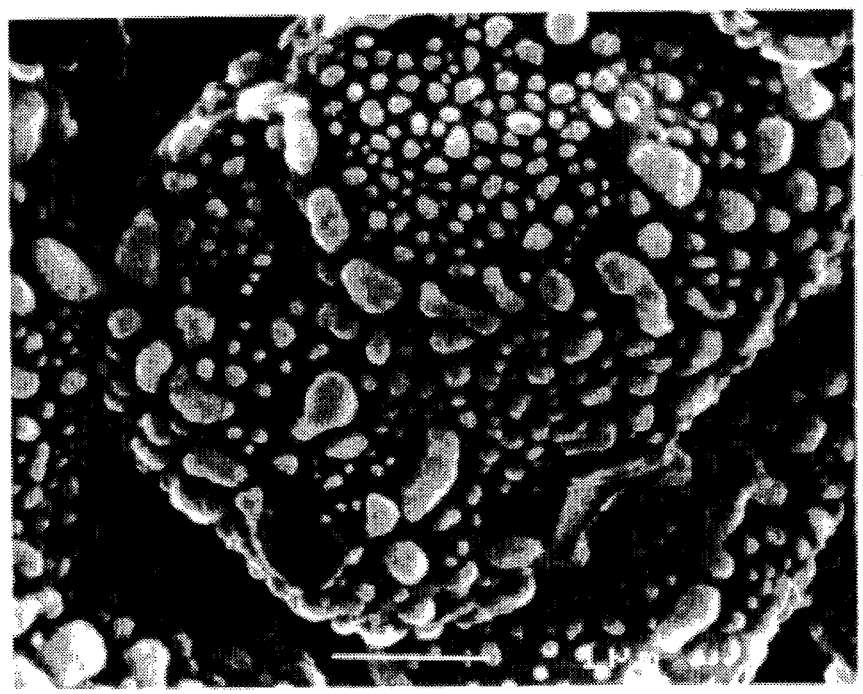
FIG. 6 is a scanning electron micrograph of a silver catalyst prepared in a similar way to that of FIG. 4 but calcined at 400° C. under air.

Preparation procedure:

Catalyst preparation was identical to example 4 except the calcination was induced in air and to a maximum temperature of 400° C. FIG. 6 is an electron micrograph of this catalyst.

The above catalysts were tested for activity and selectivity by crushing and placing 36 grams in a micro reactor consisting of a ¼" stainless steel tube which was heated in a salt bath. A feed mixture by volume of 7% oxygen, 8% $CO_2$, 15% $C_2H_4$, 70% $N_2$ was passed over the catalyst with a gas space velocity of 5500 hr$^{-1}$. The pressure was maintained at 300 psig (21.69 bar) and the temperature between 200° C. and 300° C. as required to maintain an outlet concentration of 1.5 vol % (160 Kg per hour per m³ of catalyst) ethylene oxide. The activity of the catalyst is expressed as the temperature necessary to maintain the outlet concentration of 1.50 vol % ethylene oxide, the lower the temperature, the more active the catalyst. The selectivity of the catalyst is expressed as the mol % of the total ethylene converted to ethylene oxide at the outlet concentration of 1.50 vol % ethylene. The stability of the catalyst is measured by the increase in temperature required to maintain the ethylene oxide productivity.

The results shown in following Table clearly demonstrate the superiority of the catalysts prepared in accordance with the invention, Examples 1 and 4, as compared to analogous catalyst prepared by prior art procedures.

TABLE 1

| Example # | Promoters/Levels ppm | Calcination Temp/atm. | Activity °C. | Results Sel % |
|---|---|---|---|---|
| 1 | Cs/Re/S = 420/186/32 | 400° C./N₂ | 248 | 83.7 |
| 2 | Cs/Re/S = 420/186/32 | 270° C./air | 256 | Low EO* (1.17) |
| 3 | Cs/Re/S = 420/186/32 | 400° C./air | 259 | Low EO* (1.33) |
| 4 | Cs = 300 | 400° C./N₂ | 228 | 81.5 |
| 5 | Cs = 300 | 270° C./air | 236 | 81.5 |
| 6 | Cs = 300 | 400° C./air | 238 | 81.7 |

*The catalyst were quite inactive. At temperatures close to 260° C. the amount of ethylene oxide was lower than the desired 1.5%.

I claim:

1. A process for the preparation of a supported silver catalyst suitable for use in the oxidation of ethylene to ethylene oxide wherein an inert support is impregnated with a silver/amine solution and calcined, the improvement which comprises calcining the impregnated support by heating the impregnated support to 300°–500° C. for a time sufficient to convert the silver to metallic silver and to decompose and remove organic materials, the impregnated support being maintained under an inert gas atmosphere which is essentially free of oxygen at temperatures of 250° C. or higher during the entire period of calcination.

2. The process of claim 1 wherein the impregnated support is maintained under an inert gas atmosphere at temperatures of 100° C. or higher.

3. The process of claim 1 wherein the inert gas is nitrogen.

* * * * *